(12) United States Patent
Li et al.

(10) Patent No.: US 11,335,472 B2
(45) Date of Patent: May 17, 2022

(54) SOURCE STORING APPARATUS, SOURCE GUIDING SYSTEM, AND SOURCE GUIDING METHOD

(71) Applicant: OUR UNITED CORPORATION, Xi'an (CN)

(72) Inventors: Daliang Li, Xi'an (CN); Hua Yang, Xi'an (CN)

(73) Assignee: OUR UNITED CORPORATION, Xi'an (CN)

(*) Notice: Subject to any disclaimer, the term of this patent is extended or adjusted under 35 U.S.C. 154(b) by 0 days.

(21) Appl. No.: 17/104,675

(22) Filed: Nov. 25, 2020

(65) Prior Publication Data

US 2021/0210243 A1 Jul. 8, 2021

Related U.S. Application Data

(63) Continuation of application No. PCT/CN2020/076280, filed on Feb. 21, 2020, which
(Continued)

(30) Foreign Application Priority Data

Feb. 3, 2019 (CN) .......................... 201910109125.0
Feb. 3, 2019 (CN) .......................... 201910109130.1

(51) Int. Cl.
*G21F 5/14* (2006.01)
*A61N 5/10* (2006.01)
(Continued)

(52) U.S. Cl.
CPC ................. *G21F 5/14* (2013.01); *A61N 5/10* (2013.01); *G21F 5/015* (2013.01)

(58) Field of Classification Search
CPC .............. G21F 5/14; G21F 5/015; A61N 5/10
(Continued)

(56) References Cited

U.S. PATENT DOCUMENTS 6,274,100 B1 * 8/2001 Shepherd .................. A61L 2/08
250/455.11
2017/0145305 A1 5/2017 Cohen et al.

FOREIGN PATENT DOCUMENTS

CN 107195351 9/2017
CN 108721793 11/2018
(Continued)

*Primary Examiner* — Nicole M Ippolito
(74) *Attorney, Agent, or Firm* — Emerson, Thomson & Bennett, LLC; Roger D. Emerson; Warren A. Rosborough

(57) ABSTRACT

A source storing apparatus, source guiding system and source guiding method are provided. The source storing apparatus comprises: a source tank and a shielding plug, the source tank being provided with an opening and an accommodating cavity, the accommodating cavity being configured to accommodate a cobalt source box, the shielding plug being configured to seal an opening of the accommodating cavity; wherein a first connecting structure is provided on the cobalt source box; a second connecting structure is provided on an outer side of the shielding plug, a pickup structure is provided on an inner side of the shielding plug, and the first connecting structure is detachably connected to the pickup structure. The structure of the source storing apparatus is simplified; the installation and operation processes are simple with reduced operation requirements, and are time-consuming and labor-consuming. The cost of the source guiding apparatus is also greatly reduced.

18 Claims, 6 Drawing Sheets

Related U.S. Application Data is a continuation of application No. PCT/CN2020/076281, filed on Feb. 21, 2020.

(51) Int. Cl.
*G21F 5/00* (2006.01)
*G21F 5/015* (2006.01)

(58) Field of Classification Search
USPC ......... 250/505.1, 506.1, 515.1, 516.1, 517.1, 250/518.1, 519.1
See application file for complete search history.

(56) References Cited

FOREIGN PATENT DOCUMENTS

| | | |
|---|---|---|
| CN | 109300562 | 2/2019 |
| CN | 208954644 | 6/2019 |
| CN | 209691412 | 11/2019 |
| CN | 101645316 | 2/2020 |
| CN | 210110360 | 2/2020 |

\* cited by examiner

SOURCE STORING APPARATUS, SOURCE GUIDING SYSTEM, AND SOURCE GUIDING METHOD

CROSS-REFERENCE TO RELATED APPLICATION

This application is a continuation combing the international application PCT/CN2020/076280 filed on Feb. 21, 2020, which claims priority to Chinese Application No. 201910109125.0 filed on Feb. 3, 2019, and the international application PCT/CN2020/076281 filed on Feb. 21, 2020, which claims priority to Chinese Application No. 201910109130.1 filed on Feb. 3, 2019, all of which are hereby incorporated by reference in its entireties.

TECHNICAL FIELD

The present disclosure relates to the field of radiotherapy technologies, and in particular to, a source storing apparatus, a source guiding system, and a source guiding method.

BACKGROUND

At present, for a radiotherapy device using a radioactive source box (e.g., a cobalt source box), a common source replacing approach is generally to assemble a source guiding tool outside the radiotherapy device to load and fill a radioactive source.

Because the radioactive source is radioactive, the radioactive source is stored in a source tank in transit, such that the radioactive source is shielded using the source tank. When the source is loaded, it is necessary to first take out a shielding plug of the source tank using the tool, and then take out the radioactive source in a shielded environment whilst ensuring that the source tank is shielded. In this process, ray shielding is required in all aspects, but a current source guiding tool has a complex structure, such that the installation and operation processes are complex with high operation requirements, and are time-consuming and labor-consuming. Therefore, it is necessary to provide a novel technical solution to improve one or more problems existing in the above solution.

It should be noted that the "BACKGROUND" is intended to provide a background or context for embodiments of the present disclosure provided in the appended CLAIMS. The description here is not recognized as existing technologies because of being included in the "BACKGROUND".

SUMMARY

An object of the present disclosure is to provide a source storing apparatus, a source guiding system, and a source guiding method, and then overcome, at least to a certain extent, one or more problems caused by the limitations and defects of related technologies.

According to a first aspect of the present disclosure, a source storing apparatus is provided, including: a source tank and a shielding plug, the source tank being provided with an opening and an accommodating cavity, the accommodating cavity being configured to accommodate a cobalt source box, the shielding plug being configured to close an opening of the accommodating cavity; where a first connecting structure is provided on the cobalt source box;

a second connecting structure is provided on an outer side of the shielding plug, a pickup structure is provided on an inner side of the shielding plug, and the first connecting structure is detachably connected to the pickup structure.

An embodiment of the present disclosure further provides a source guiding system configured to guide a cobalt source box from a first source storing apparatus into a second source storing apparatus, where the first source storing apparatus or the second source storing apparatus is a source storing apparatus provided in embodiments of the present disclosure; and the cobalt source box further includes a third connecting structure; and the source guiding system including: a source guiding tank, the source guiding tank including a tank body, a first pull rod and a first opening, a second pull rod and a second opening, where the tank body includes a source-carrying cavity, the first pull rod and the first opening are located on opposite sides of the source-carrying cavity along a first direction, the second pull rod and the second opening are located on opposite sides of the source-carrying cavity along a second direction, the first pull rod moves along the first direction and is connectable to a second connecting structure of a shielding plug of the first source storing apparatus; and the second pull rod moves along the second direction and is connectable to a third connecting structure of the cobalt source box.

An embodiment of the present disclosure further provides a source guiding method, being applied to a source guiding system according to any one embodiment of the present disclosure and used for guiding a cobalt source box from a source storing apparatus into a radiotherapy device. The method includes:

connecting a first connecting structure of the cobalt source box and a pickup structure of a shielding plug of the source storing apparatus;

driving a first pull rod to connect the first pull rod to a second connecting structure of the shielding plug of the source storing apparatus, and lifting the shielding plug to a source-carrying cavity of a source guiding tank;

driving a second pull rod to connect the second pull rod to a third connecting structure of the cobalt source box;

driving the first pull rod to coordinate with the second pull rod, such that the first connecting structure of the cobalt source box is separated from the pickup structure; and driving the second pull rod to send the cobalt source box into the radiotherapy device and fix the cobalt source box with the radiotherapy device.

An embodiment of the present disclosure further provides a source guiding method, being applied to a source guiding system provided in embodiments of the present disclosure and used for guiding a cobalt source box from a radiotherapy device into a source storing apparatus. The method includes:

driving a first pull rod to connect the first pull rod to a second connecting structure of a shielding plug of the source storing apparatus, and lifting the shielding plug to a source-carrying cavity of a source guiding tank;

driving a second pull rod to connect the second pull rod to a third connecting structure of the cobalt source box, and pulling the cobalt source box to the source-carrying cavity of the source guiding tank;

driving the first pull rod to coordinate with the second pull rod, such that the first connecting structure of the cobalt source box is connected to a pickup structure;

driving the second pull rod to separate the second pull rod from the cobalt source box; and driving the first pull rod to send the cobalt source box into the source storing apparatus.

The technical solutions provided in the embodiments of the present disclosure may include the following beneficial effects:

The present disclosure provides a source storing apparatus, a source guiding system, and a source guiding method. The source storing apparatus includes: a source tank and a shielding plug, a pickup structure is provided on the shielding plug, and a first connecting structure is provided on a cobalt source box. Then, the cobalt source box is connected to the shielding plug through the first connecting structure and the pickup structure, thereby taking out the shielding plug and the cobalt source box once during the source replacement, simplifying the operating apparatus and operation steps, and improving the operation safety. Through the above radioactive source guiding system and method, the structure of the source guiding tool is simplified; the installation and operation processes are simple with reduced operation requirements, and are time-consuming and labor-consuming; and the cost of the source guiding tool is also greatly reduced.

Figure 1:
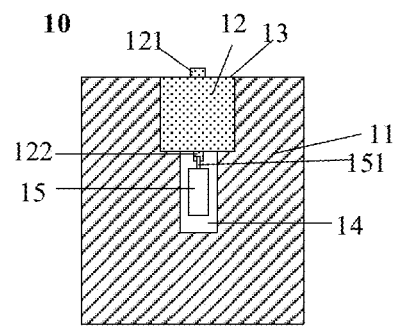
FIG. 1 is a schematic diagram of a source storing apparatus in the present disclosure.

It is noted that the elements shown in the figures may not be in proper proportion to each other.

DETAILED DESCRIPTION

Example embodiments will now be described more comprehensively with reference to the accompanying drawings. However, the example embodiments can be implemented in various forms, and should not be construed as being limited to the examples set forth herein; on the contrary, these embodiments are provided to make the present disclosure more comprehensive and complete, and fully convey the concept of the example embodiments to those skilled in the art. The described features, structures, or characteristics may be combined in one or more embodiments in any suitable manner.

In addition, the accompanying drawings are only schematic illustrations of the present disclosure, and are not necessarily drawn to scale. Identical reference numerals in the accompanying drawings represent identical or similar portions, and therefore repeated descriptions thereof will be omitted. Some of the block diagrams shown in the drawings are functional entities, and do not necessarily correspond to physically or logically independent entities.

An embodiment of the present disclosure discloses a source storing apparatus 10. For example, as shown in FIG. 1, the source storing apparatus includes: a source tank 11 and a shielding plug 12, the source tank 11 is provided with an opening and an accommodating cavity 14, the accommodating cavity 14 is configured to accommodate a cobalt source box 15, the shielding plug 12 is configured to seal an opening of the accommodating cavity 14; where a first connecting structure 151 is provided on the cobalt source box 15; a second connecting structure 121 is provided on an outer side of the shielding plug 12, a pickup structure 122 is provided on an inner side of the shielding plug, and the first connecting structure 151 is detachably connected to the pickup structure 122.

For example, in the embodiment of the present disclosure, the first connecting structure may be detachably connected to the pickup structure by a threaded connection or by a buckled connection. The specific structure and connection mode thereof are not limited in embodiments of the present disclosure. In the embodiment of the present disclosure, the second connecting structure is provided on the outer side of the shielding plug, and the second connecting structure may be connected to a pull rod of a source guiding system, thereby taking out the shielding plug and the cobalt source box simultaneously through the pull rod of the source guiding system. The connection mode between the second connecting structure and the pull rod is not limited in the embodiments of the present disclosure, e.g., may be a threaded connection or a snap fit.

For a source storing apparatus provided in an embodiment of the present disclosure, a pickup structure is provided on the shielding plug, a first connecting structure is provided on a cobalt source box, and the cobalt source box is connected to the shielding plug through the first connecting structure and the pickup structure, thereby taking out the shielding plug and the cobalt source box once during the source replacement, simplifying the operating apparatus and operation steps, and improving the operation safety. The source storing apparatus in the embodiment of the present disclosure, e.g., may be a source tank.

Figure 2:
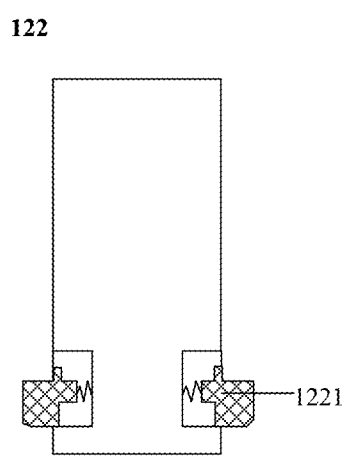
FIG. 2 is a schematic structural diagram of a pickup structure in the present disclosure.

In a source storing apparatus provided in an embodiment of the present disclosure, for example, as shown in FIG. 2, the pickup structure 122 includes an elastic member 1221, the elastic member 1221 is snapped into the first connecting structure to realize a connection between the cobalt source box and the shielding plug. The pickup structure includes the elastic member, such that an external force may be applied to achieve a snap-fit of the elastic member, thereby facilitating the connection between and operation of the pickup structure and the first connecting structure. A specific structure of the elastic member is not limited in the embodiments of the present disclosure, and is described only with FIG. 2 as an example. Further, a plurality of, e.g., three or four, elastic members may be provided.

For example, in a source storing apparatus provided in an embodiment of the present disclosure, the pickup structure 122 is directly and fixedly connected to the shielding plug 12. Alternatively, the pickup structure 122 is connected to the shielding plug 12 by a connecting rod. When the pickup structure is directly fixed on the shielding plug, a space of the pickup structure can be reduced. The connection between the pickup structure and the shielding plug may be determined based on specific settings of the source storing apparatus, and is not limited in the embodiments of the present disclosure.

Figure 3:
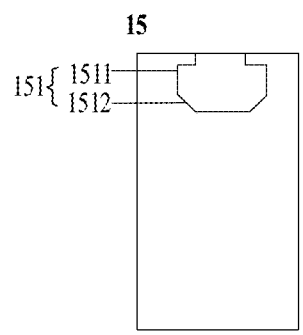
FIG. 3 is a schematic diagram of a connecting structure of a cobalt source box in the present disclosure.
Figure 4:
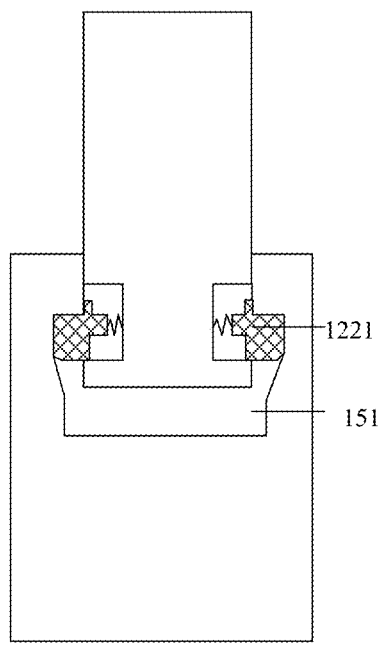
FIG. 4 is schematic diagram of a connection between a pickup structure and a cobalt source box of the present disclosure.

In a source storing apparatus provided in an embodiment of the present disclosure, as shown in FIG. 3, the first connecting structure 151 is a connecting slot. As shown in FIG. 4, the pickup structure 122 is snappable into the connecting slot. Specifically, the elastic member 1221 is snappable into the connecting slot.

Figure 5:
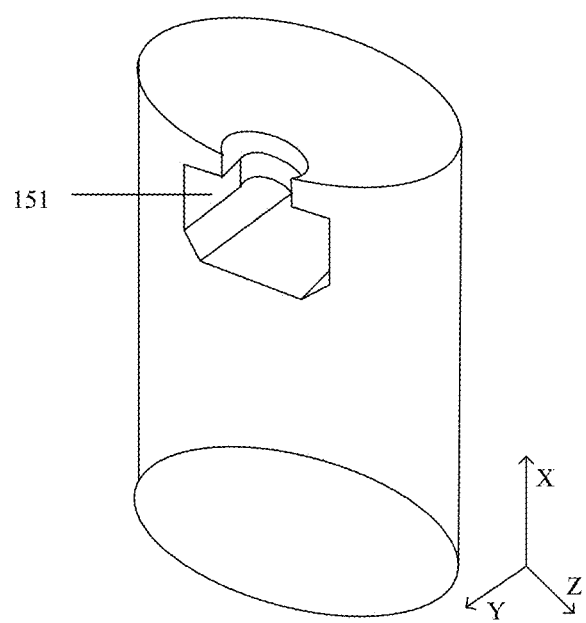
FIG. 5 is a schematic diagram of a connecting structure of a cobalt source box in the present disclosure.

In a schematic diagram of a cobalt source box provided in an embodiment of the present disclosure, a connecting slot of the cobalt source slot includes a first opening and a second opening that are in communication, where the first opening is located in a first direction (e.g., X direction), and the second opening is located in a second direction (e.g., Y direction). As shown in FIG. 5, the first opening may be located at a top opening of the cobalt source box, and the second opening may be a side opening of the cobalt source box. The pickup structure may extend from the first opening into the connecting slot to be snapped to the connecting slot, and separate from the connecting slot from the second opening. It should be noted that FIG. 5 only illustrates the connecting slot of the cobalt source box, and does not show other structures of the cobalt source box.

In the source storing apparatus provided in an embodiment of the present disclosure, as shown in FIG. 3, the connecting slot includes a clamping slot 1511 and a compressing slot 1512, where a maximum size of the clamping slot 1511 is larger than that of the first opening. The pickup structure is an elastic member, and a size of the clamping slot may be larger than or equal to a maximum size of the elastic member when the elastic member is not compressed, such that the elastic member is clampable within the clamping slot.

For example, when the pickup structure includes the elastic member, the first opening is larger than a minimum compression size of the elastic member and smaller than a maximum extension size of the elastic member, so as to help the elastic member enter the connecting slot from the first opening, and prevent the elastic member from disengaging from the first opening. For example, a maximum size of the clamping slot is larger than the maximum extension size of the elastic member, to better implement the clamped connection. For example, a maximum size of the compressing slot is smaller than the maximum extension size of the elastic member, such that the elastic member separates from the second opening after being compressed at a position of the compressing slot.

In an embodiment of the present disclosure, in order to prevent the pickup structure from separating from the cobalt source box, a bottom size of the second opening is larger than a top size of the second opening, and a maximum opening size of the second opening is larger than or equal to a minimum compression size of the pickup structure.

In order to contributing more to compressing the elastic member at the second opening, such that the pickup structure separates, a size of the second opening at a position corresponding to the compressing slot is larger than or equal to the minimum compression size of the pickup structure in an embodiment of the present disclosure.

An embodiment of the present disclosure provides a source guiding system configured to guide a cobalt source box from a first source storing apparatus into a second source storing apparatus, where the first source storing apparatus or the second source storing apparatus is a source storing apparatus provided in embodiments of the present disclosure; where the first source storing apparatus may be a source storing apparatus provided in the embodiments of the present disclosure, the second source storing apparatus may be a radiotherapy device, and the guiding a cobalt source box from a first source storing apparatus into a second source storing apparatus is loading a radioactive source into the radiotherapy device; or the first source storing apparatus is a radiotherapy device, the second source storing apparatus is a source storing apparatus provided in the embodiments of the present disclosure, and the guiding a cobalt source box from a first source storing apparatus into a second source storing apparatus is taking out a radioactive source from the radiotherapy device and loading the radioactive source into a source tank. In an embodiment of the present disclosure, description is provided, e.g., with the first source storing apparatus being a source storing apparatus provided in the embodiments of the present disclosure, e.g., a source tank, and with the second source storing apparatus being a radiotherapy device as an example.

Figure 6:
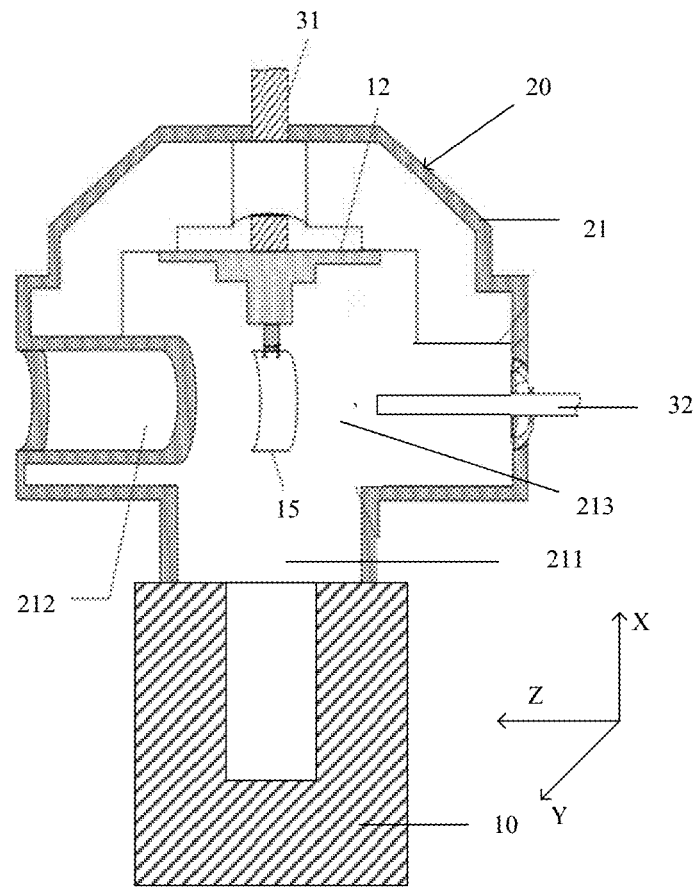
FIG. 6 is a schematic diagram of a source guiding system in the present disclosure.

The source guiding system includes: a source guiding tank 20. As shown in FIG. 6, the source guiding tank 20 includes a tank body 21, a first pull rod 31 and a first opening 211, a second pull rod 32 and a second opening 212, where the tank body 21 includes a source-carrying cavity 213, the first pull rod 31 and the first opening 211 are located on opposite sides of the source-carrying cavity 213 along a first direction (e.g., X direction shown in FIG. 6), the second pull rod 32 and the second opening 212 are located on opposite sides of the source-carrying cavity 213 along a second direction (e.g., Z direction shown in FIG. 6), and the first pull rod 31 moves along the first direction and is connectable to a second connecting structure of the shielding plug 12 of the first source storing apparatus 10. In the source guiding system provided in the embodiment of the present disclosure, the cobalt source box further includes a third connecting structure; and the second pull rod 32 moves along the second direction and is connectable to the third connecting structure of the cobalt source box 15.

In the source guiding system provided in the embodiment of the present disclosure, the first opening corresponds to a position of the first source storing apparatus, and then may be connected to the shielding plug through the first pull rod. The shielding plug may be connected to the cobalt source box, and then when the first pull rod is pulled up, the shielding plug and the cobalt source box can be pulled out together, such that the cobalt source box is located within the source-carrying cavity of the source guiding tank. The second opening corresponds to a source loading port of the radiotherapy device. After the second pull rod is connected to the cobalt source box, the shielding plug is disconnected from the cobalt source box, and the cobalt source box is sent into the radiotherapy device using the second pull rod, thus completing the source loading process.

Likewise, when the cobalt source box needs to be taken out from the radiotherapy device, the second pull rod may be first connected to the cobalt source box, such that the cobalt source box is located within the source-carrying cavity of the source guiding tank. Then, the cobalt source box is connected to the shielding plug, and is loaded into the first source storing apparatus through the first pull rod. Then, the first pull rod is disconnected from the shielding plug, to realize the source removal process.

For example, the connection between the cobalt source box and the shielding plug is disconnectable as described above. The source storing apparatus provided in the embodiment of the present disclosure may be referred to, which may be provided with the pickup structure on the shielding plug, and is snapped to the connecting slot on the cobalt source box. The pickup structure includes the elastic member. Specifically, as shown in FIG. 5 and FIG. 6, when the first pull rod is driven, such that the shielding plug moves downward along the X direction, the elastic member is clamped into the connecting slot of the cobalt source box, thereby realizing the connection between the shielding plug and the cobalt source box. The second pull rod is connected to the cobalt source box. When the shielding plug continues moving downward along the X direction, the elastic member is compressed at the position of the compressing slot. In this case, the second pull rod may be driven to move outward, such that the elastic member separates from the cobalt source box from the second opening, and then the cobalt source box is sent into the radiotherapy device through the second pull rod. The source removal process is the same as the source loading principle. The description will not be repeated here.

The source guiding system provided in the embodiment of the present disclosure includes the source storing apparatus provided in the embodiment of the present disclosure. The source storing apparatus coordinates with the source guiding tank to realize the removal and assembly of the radioactive source, and no other shielding apparatus is required during the removal and assembly, thereby simplifying the radioactive source removal and assembly process, and improving the safety of the removal and assembly of the radioactive source.

For example, in the embodiment of the present disclosure, the first direction is perpendicular to the second direction.

In the source guiding system provided in the embodiment of the present disclosure, the source guiding system further includes a first shielding door configured to open and close the first opening; and/or, the source guiding system further includes a second shielding door configured to open and close the second opening.

Specifically, the source guiding system may merely include the first shielding door, or the source guiding system may merely include the second shielding door, or the source guiding system may include both the first shielding door and the second shielding door. The source guiding system includes the shielding door, to further improve the shielding safety of the source guiding system.

In the source guiding system provided in the embodiment of the present disclosure, the first pull rod and/or the second pull rod are/is provided with a limiting slot, and the source guiding system further includes a fastener fixable with the limiting slot to prevent the first pull rod and/or the second pull rod from rotating. For example, the first pull rod is provided with a limiting slot. After the first pull rod lifts the shielding plug and the cobalt source box to the source-carrying cavity, the fastener is inserted into the limiting slot, to prevent the shielding plug and the cobalt source box from rotating in the source-carrying cavity, and facilitate the connection between the second pull rod and the cobalt source box.

In the source guiding system provided in the embodiment of the present disclosure, a glass window is provided on the source guiding tank; or a camera and/or a detection lamp are/is further provided within the source-carrying cavity of the source guiding tank, such that an operator can see the inside of the source-carrying cavity from the outside, so as to realize, e.g., connection or removal by adjusting the position of the pull rod.

For example, in the source guiding system in the embodiment of the present disclosure, the source guiding tank includes a plurality of components, and the plurality of components is fixedly connected. For example, the source guiding tank includes a source guiding shield and a shielding cover, to facilitate the processing and transport of the source guiding tank.

A source guiding method provided in an embodiment of the present disclosure is applied to a source guiding system provided in embodiments of the present disclosure, and is used for guiding a cobalt source box from a source storing apparatus into a radiotherapy device, i.e., a first source storing apparatus is a source storing apparatus provided in the embodiments of the present disclosure, and a second source storing apparatus is a radiotherapy device, i.e., the guiding a cobalt source box from a first source storing apparatus into a second source storing apparatus is loading a radioactive source into the radiotherapy device. The method includes:

Step 101: connecting a first connecting structure of a cobalt source box and a pickup structure of a shielding plug of a source storing apparatus. Step 101 may realize the connection in other ways, e.g., realize the connection through a hot cell, or realize the connection through the source storing apparatus in the embodiments of the present disclosure. Description is provided below, e.g., with realizing the connection through the source storing apparatus in the embodiments of the present disclosure as an example.

As shown in FIG. 6, the first connecting structure may be fixedly connected to the shielding plug 12 using the first pull rod 31, and then the shielding plug 12 moves downward using the pull rod, thereby the elastic member is snapped on the shielding plug 12 to the connecting slot on the cobalt source box 15, i.e., realizing the connection between the first connecting structure of the cobalt source box and the pickup structure of the shielding plug of the source storing apparatus.

Step 102: driving a first pull rod to connect the first pull rod to a second connecting structure of the shielding plug of the source storing apparatus, and lifting the shielding plug to a source-carrying cavity of a source guiding tank. The driving the first pull rod may be implemented by motor drive or by manual pull. This is not limited in the embodiments of the present disclosure.

Step 103: driving a second pull rod to connect the second pull rod to a third connecting structure of the cobalt source box. For example, the second pull rod may be threadedly connected to the cobalt source box, and the second pull rod is driven to rotate, thereby connecting a thread of the second pull rod to a threaded hole on the cobalt source box. Of course, a specific connection mode of the second pull rod and the third connecting structure is not limited in the embodiments of the present disclosure, and is merely illustrated with the above description as an example.

Step 104: driving the first pull rod to coordinate with the second pull rod, such that the first connecting structure of the cobalt source box separates from the pickup structure.

For example, step 104 specifically includes: driving the first pull rod to move along a first direction such that an elastic member is in a compressing slot; and driving the second pull rod to move along a second direction, such that the pickup structure separates from a connecting slot from a second opening.

Specifically, as shown in FIG. 5 and FIG. 6, when the first pull rod is driven, such that the shielding plug moves downward along the X direction, the elastic member is clamped into the connecting slot of the cobalt source box, thereby realizing the connection between the shielding plug and the cobalt source box. The second pull rod is connected to the cobalt source box. When the shielding plug continues moving downward along the X direction, the elastic member is compressed at the position of the compressing slot. In this case, the second pull rod may be driven to move outward, such that the elastic member separates from the cobalt source box from the second opening.

Step 105: driving the second pull rod to send the cobalt source box into the radiotherapy device and fix the cobalt source box with the radiotherapy device.

The source guiding method provided in the embodiment of the present disclosure can realize the source removal and assembly only using the source guiding tank without the need of using other shielding apparatus, thereby simplifying the source guiding process and improving the source guiding safety.

After sending the cobalt source box into the radiotherapy device, the source guiding method provided in the embodiment of the present disclosure further includes: driving the radiotherapy device to switch off and shield a radioactive source, i.e., directly switching off the source using the radiotherapy device, such that the operator removes, e.g., the source guiding tank.

Of course, the source guiding method provided in the embodiment of the present disclosure further includes a process of taking out the radioactive source from the radiotherapy device and storing the radioactive source in the source storing apparatus. The principle of the process is similar to the above.

An embodiment of the present disclosure discloses a source guiding method. The source guiding method is applied to a source guiding system in the embodiments of the present disclosure, and is used for guiding a cobalt source box from a radiotherapy device into a source storing apparatus. The method includes:

Step 201: driving a first pull rod to connect the first pull rod to a second connecting structure of the shielding plug of the source storing apparatus, and lifting the shielding plug to a source-carrying cavity of a source guiding tank.

Step 202: driving a second pull rod to connect the second pull rod to a third connecting structure of the cobalt source box, and pulling the cobalt source box to the source-carrying cavity of the source guiding tank.

Step 203: driving the first pull rod to coordinate with the second pull rod, such that the first connecting structure of the cobalt source box is connected to the pickup structure.

Step 204: driving the second pull rod to separate the second pull rod from the cobalt source box.

Step 205: driving the first pull rod to send the cobalt source box into the source storing apparatus.

That is, when the cobalt source box needs to be taken out from the radiotherapy device, the second pull rod may be first connected to the cobalt source box, such that the cobalt source box is located within the source-carrying cavity of the source guiding tank. Then, the cobalt source box is connected to the shielding plug, and is loaded into the first source storing apparatus through the first pull rod. Then, the first pull rod is disconnected from the shielding plug, to realize the source removal process.

Figure 7:
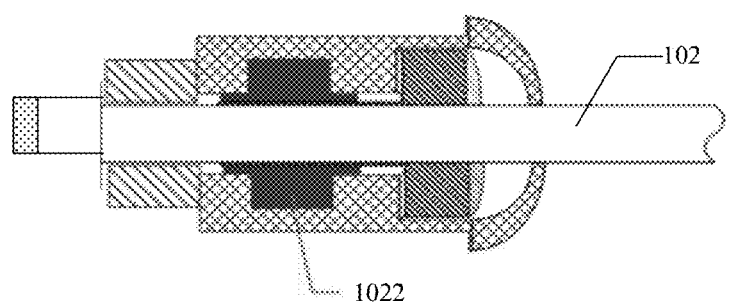
FIG. 7 and FIG. 8 show a schematic structural diagram of a pull rod in an example embodiment of the present disclosure.
Figure 8:
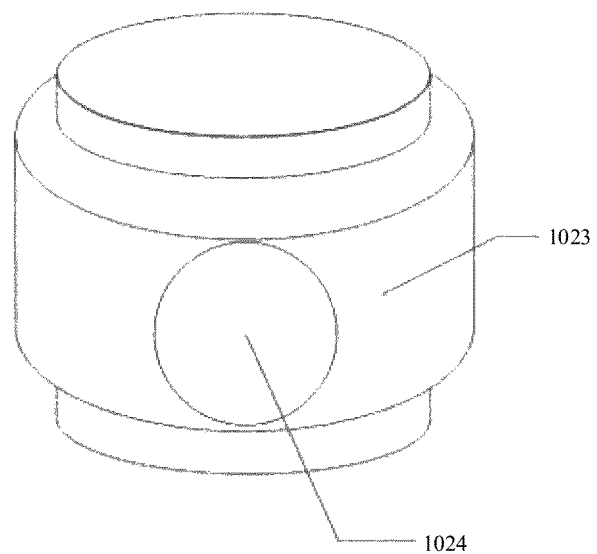
Figure 9:
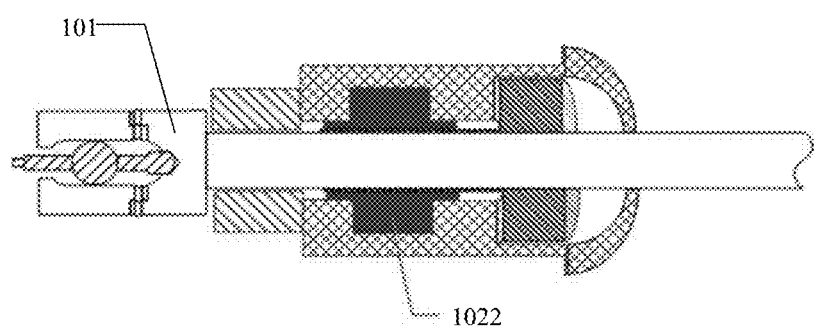
FIG. 9 shows a schematic structural diagram of an adjusting member in an example embodiment of the present disclosure.

For example, FIG. 7 and FIG. 8 show a schematic structural diagram of a pull rod in an example embodiment of the present disclosure. FIG. 9 shows a schematic structural diagram of an adjusting member in an example embodiment of the present disclosure. The present disclosure provides a pull rod. As shown in FIG. 7, FIG. 8, and FIG. 9, the pull rod includes: a rod-shaped part 102 and an adjusting member 1012. The rod-shaped part 102 includes a pickup end and an operation end; and the adjusting member 1012 is located between the pickup end and the operation end of the rod-shaped part 102. For example, as shown in FIG. 8, the adjusting member 1012 includes a cambered surface, and the rod-shaped part 102 runs through the cambered surface 1023.

An embodiment of the present disclosure provides a pull rod. The pull rod is connected to the adjusting member, and is adjustable and swingable along a direction of the cambered surface of the adjusting member, thereby improving the connection flexibility of the pull rod. For example, the pull rod may be a second pull rod.

For example, the adjusting member 1022 may be spherical, or the adjusting member 1022 may be cylindrical. The adjusting member 1022 and the rod-shaped part 102 may be integrated, or the adjusting member 1022 is provided with an opening 1024, and the rod-shaped part 102 runs through the opening 1024. When the rod-shaped part 102 runs through the adjusting member 1022, the adjusting member 1022 may be fixedly connected to the rod-shaped part 102 by, but not limited to, a pin, to prevent the rod-shaped part 102 from rotating with respect to the adjusting member 1022. When the rod-shaped part is rotating, the rod-shaped part 102 is rotatable along the direction of the cambered surface 1023, thereby improving the flexibility of the pull rod.

Figure 10:
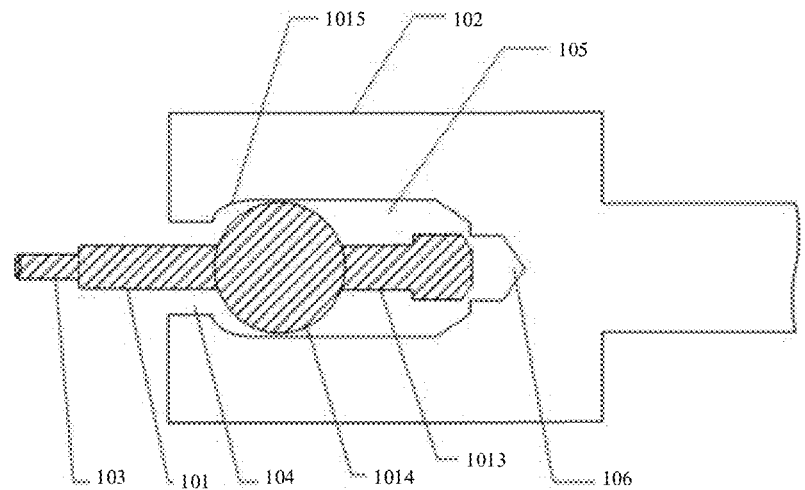
FIG. 10 shows a schematic structural diagram of a pull rod in an example embodiment of the present disclosure.

An embodiment of the present disclosure provides a pull rod. As shown in FIG. 9 and FIG. 10, the pull rod further includes a connector 101 and a rod-shaped part 102, where:

a front end of the connector 101 is provided with a connecting structure 103; and the rod-shaped part 102 is provided with an opening 104 and an accommodating space 105, the connector 101 is provided in the accommodating space 105 of the rod-shaped part 102, the connecting structure 103 of the connector extends from the opening of the rod-shaped part into the accommodating space 105, the rod-shaped part 102 and a contactable part at a tail end of the connector are provided with a limiting structure 106, and the tail end of the connector 101 is movably assembled with the limiting structure 106, to limit the movement of the connector when the limiting structure is assembled with the tail end of the connector. The "movable" in this embodiment means that when the rod-shaped part is pushed toward the connector, the limiting structure can be assembled with the tail end of the connector; while when the rod-shaped part is away from the connector, the limiting structure can be removed from the tail end of the connector.

An embodiment of the present disclosure provides a pull rod. When the rod-shaped part moves such that the limiting structure 106 is assembled and connected with the tail end of the connector, the rod-shaped part can be rotated to drive the connector to rotate; or the rod-shaped part can be moved to drive the connector to move, thereby connecting the connecting structure 103 of the connector to an external apparatus, e.g., a cobalt source box. When a relative position between the connecting structure 103 of the connector and the cobalt source box needs to be adjusted, the rod-shaped part can be pulled away from the cobalt source box, such that the tail end of the connector separates from the limiting structure 106 of the rod-shaped part 102, and then the pull rod is rotated or swung to adjust the relative position between the connecting structure 103 of the connector and the cobalt source box, thereby improving the flexibility and accuracy of the pull rod.

For example, the front end of the connector 101 may be an end of the connector 101 close to a source carrier 107 of the source guiding apparatus. The connecting structure 103 may include a threaded connection unit configured to be threadedly connected to the source carrier 107. The source carrier 107 may include a threaded connection hole matching the threaded connection unit. When the connecting structure 103 is pushed to the vicinity of the source carrier 107, the threaded connection unit is aligned with the threaded connection hole, and the threaded connection unit is screwed into the threaded connection hole. For example, the rod-shaped part 102 may be rotated to drive the threaded connection unit to rotate, such that the threaded connection unit is screwed into the threaded connection hole. The threaded connection has a high reliability, can prevent the source carrier 107 from falling during the pushing and pulling, and can further prevent the radioactive source from leaking.

Specifically, the tail end of the connector 101 refers to an end of the connector 101 close to the limiting structure 106. When the limiting structure 106 is assembled with the tail end of the connector, movement of the connector 101 can be limited. When the rod-shaped part 102 is pushed toward the connector 101, the limiting structure 106 can be assembled with the tail end of the connector; while when the rod-shaped part 102 is away from the connector 101, the limiting structure 106 can be removed from the tail end of the connector. For example, another pull rod 108 of the source guiding apparatus can lift the source carrier 107 from a source guiding tank 109 of the source guiding apparatus to an accommodating cavity 1010 of the source guiding apparatus. In this embodiment, the source carrier 107 is connected to a lead plug 1012 of the source guiding tank, the other pull rod 108 is externally connected to the lead plug 1012, the lead plug 1012 together with the source carrier 107 can be lifted to the accommodating cavity 1010 through the other pull rod 108, and then the rod-shaped part 102 can be pushed, such that the connector 1011 is close to the source carrier 107. When the connecting structure 103 of the connector 101 contacts with the source carrier 107, the tail end of the connector is assembled with the limiting structure 106 because of being blocked by the source carrier 107. In this case, the rod-shaped part 102 can be rotated to drive the connector 101 to be threadedly connected to the source carrier 107. Of course, the rod-shaped part 102 can be pulled backward, and the connecting structure 103 can separate from the limiting structure 106.

In an embodiment, the connector 101 may further include a connecting rod 1013 and a swinging member 1014 located between a front end and a tail end of the connecting rod. A contact surface between the swinging member 1014 and the accommodating space 105 is an arc surface, the connector is rotatable along an arc surface of the swinging member, a diameter of the swinging member 1014 is larger than a maximum diameter of the connecting rod 1013, and the swinging member 1014 is in the accommodating space 105 of the rod-shaped part.

Specifically, a front end of the connecting rod refers to an end of the connecting rod 1013 close to the connecting structure 103, and a tail end of the connecting rod refers to an end of the connecting rod 1013 close to the limiting structure 106. The arc surface of the swinging member 1014 matches a shape of the accommodating space 105, and in order to realize a function of the swinging member 1014 driving the connecting rod 1013 to rotate, the diameter of the swinging member 1014 may be larger than the maximum diameter of the connecting rod 1013.

For example, the swinging member 1014 may be cylindrical or spherical. In FIG. 10, the swinging member 1014 being spherical is taken as an example. The swinging member may also be cylindrical as shown in FIG. 8, in which the rod-shaped part runs through a through hole of the swinging member.

Specifically, in order to prevent the connector 101 from separating from the accommodating space 105, the diameter of the swinging member 1014 may be larger than a maximum diameter of the opening 104.

Specifically, the swinging member 1014 and the connecting rod 1013 may be integrated, or the connecting rod 1013 may run through the swinging member 1014. When the connecting rod 1013 runs through the swinging member 1014, the connecting rod 1013 may be fixedly connected to the swinging member 1014 by, but not limited to, a pin, to prevent the swinging member 1014 from rotating with respect to the connecting rod 1013.

Specifically, an inner wall of the accommodating space 105 may be arc-shaped, and the arc surface of the swinging member 1014 may match the arc-shaped inner wall of the accommodating space 105. A front end of the accommodating space 105 may include an arc-shaped slot 1015. The front end of the accommodating space 105 refers to an end of the accommodating space 105 close to the opening 104. In order to achieve a better rotation effect of the connector 101, the arc-shaped slot 1015 can match the arc surface of the swinging member 1014.

Figure 11A:
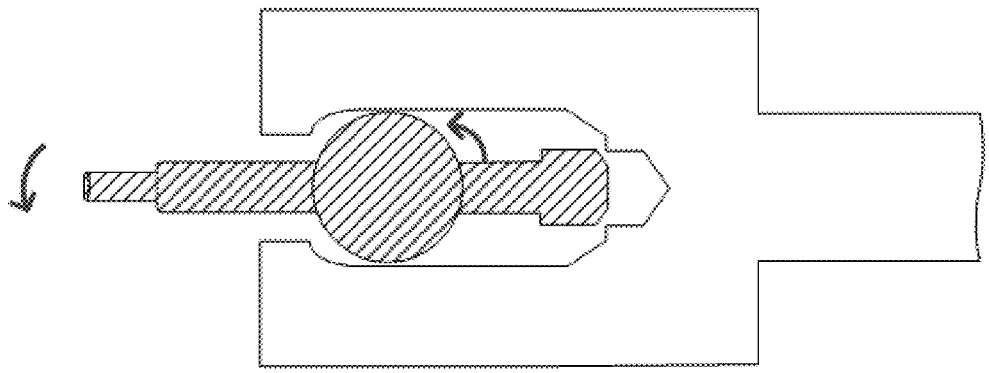
FIG. 11A shows a working principle diagram of a connector in an example embodiment of the present disclosure.
Figure 11B:
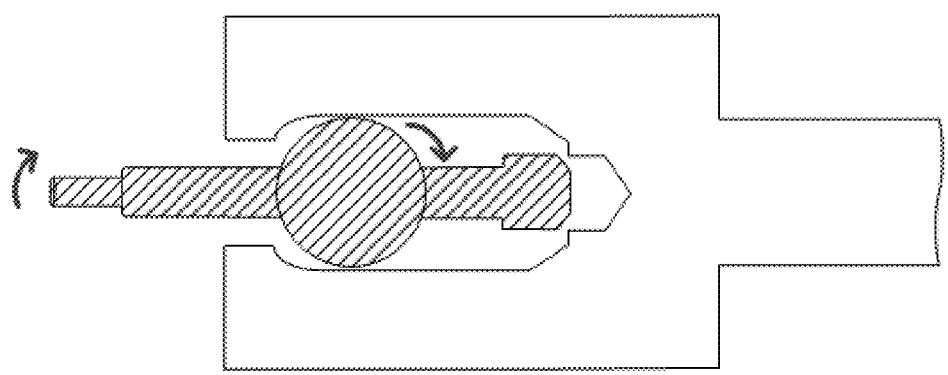
FIG. 11B shows a working principle diagram of a connector in an example embodiment of the present disclosure.

In this embodiment, when the limiting structure 106 is removed from the tail end of the connector, the connector 101 can swing along the arc surface of the swinging member 1014. For example, as shown in FIG. 11A, FIG. 11A is a working principle diagram of a connector. When the connector 101 rotates in a counterclockwise direction, the source carrier 107 can be driven to move downward within a certain range. As shown in FIG. 11B, FIG. 11B is a working principle diagram of a connector. When the connector 101 rotates in a clockwise direction, the source carrier 107 can be driven to move upward within a certain range. When the swinging member 1014 is spherical, the rotation direction of the swinging member 1014 may be 360°. The rotation direction of the spherical swinging member is not limited in this embodiment in any way. When the pull rod is pushed to connect the source carrier 107 to the pull rod, the connector 101 is movable within a certain range, such that the source carrier 107 is connected to the pull rod.

In the embodiment of the present disclosure, on the one hand, the connecting rod is connected to the source carrier 107 by a threaded connection, thereby preventing the source carrier 107 from falling, and improving the safety of the source replacement operation.

Figure 12:
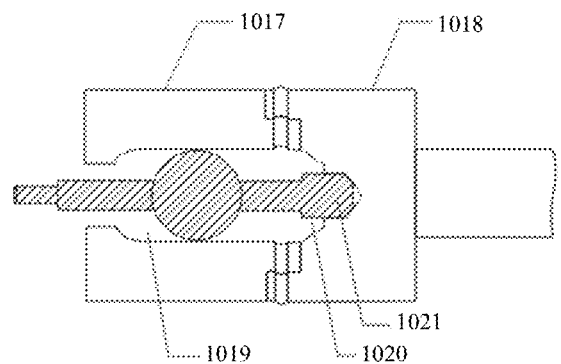
FIG. 12 is a schematic structural diagram of a pull rod.

In another embodiment, as show in FIG. 12, FIG. 12 is a schematic structural diagram of a pull rod. The rod-shaped part 102 may include a first rod-shaped part 1017 and a second rod-shaped part 1018 that are connected and fixed, and a front end of the first rod-shaped part 1017 is provided with the opening 104.

Specifically, in order to facilitate the installation and replacement of the connector 101, an opening at a tail end of the first rod-shaped part 1017 may be larger than a maximum size of the connector 101, and the first rod-shaped part 1017 and the second rod-shaped part 1018 may be connected by, but not limited to, a connection mode, such as a buckle, or a pin, or may be integrated.

For example, the first rod-shaped part 1017 may include a first accommodating cavity 1019, the second rod-shaped part 1018 may include a second accommodating cavity 1020, the limiting structure 106 may be provided within the second accommodating cavity 1020, and the first accommodating cavity 1019 and the second accommodating cavity 1020 constitute an accommodating space 105. For example, the limiting structure 106 may be provided on the second rod-shaped part 1018.

For example, the limiting structure 106 may be a limiting slot, which is located within the second accommodating cavity 1020. The tail end of the connector 101 may further include a limiting unit 1021, and the limiting slot may be assembled with the limiting unit 1021. In an embodiment of the present disclosure, the limiting slot may be a quadrangular limiting slot or a hexagonal limiting slot. Accordingly, the limiting structure is quadrangular or hexagonal. In the embodiment of the present disclosure, the limiting slot and the limiting structure can prevent the connector from moving after being limited, and the specific structures and shapes of the limiting slot and the limiting structure are not limited.

In an embodiment, a limiting slot may be provided on the surface of an end of the rod-shaped part 102 away from the connector 101, and a pin matching the limiting slot may be provided on the source guiding apparatus to prevent the rod-shaped part 102 from rotating when being pushed.

In an embodiment, the rod-shaped part 102 may include at least 2 pull rods connected in sequence; where a diameter of each pull rod is increased successively from a pull rod connected to the connector 101. When diameters of two adjacent pull rods are different, radiation can be effectively shielded. When the diameter of each pull rod is increased successively from the pull rod connected to the connector 101, the radiation shielding effect is better.

In an embodiment, at least one pull rod connected to the connector 101 among the at least 2 pull rods is made of a tungsten alloy. Because the tungsten alloy has high density and high shielding performance, the radiation shielding effect is better when at least one pull rod connected to the connector 101 is made of the tungsten alloy.

Figure 13:
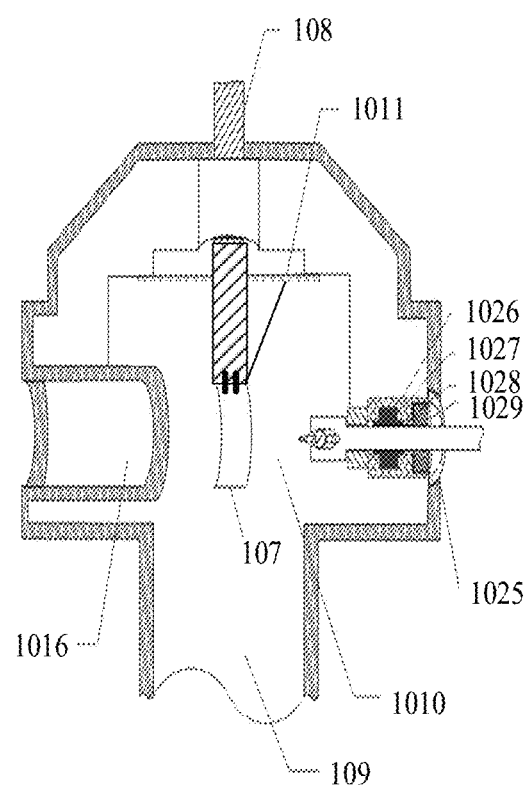
FIG. 13 shows a schematic structural diagram of a source guiding apparatus in an example embodiment of the present disclosure.

This example embodiment further provides a source guiding apparatus. As show in FIG. 13, FIG. 13 is a schematic structural diagram of a source guiding apparatus. The source guiding apparatus may include the source guiding tank 109 and the pull rod in the above embodiments, where:

the source guiding tank 109 includes an accommodating cavity 1010 capable of accommodating the source carrier 107; and a hole site 1025 is provided on the source guiding tank 109, and the pull rod can enter the accommodating cavity 1010 through the hole site 1025.

For example, a shielding member 1026 is further included between the source guiding tank and the pull rod, and the pull rod is fixedly arranged with the source guiding tank 109 through the shielding member 1026.

For example, the shielding member 1026 may include a base body 1027 and a tubular unit 1028, where an end of the base body 1027 has a groove, and a bottom surface of the groove has a through hole extending along an axial direction of the base body. The adjusting member 1022 is arranged within the through hole, the adjusting member 1022 is coaxial with the through hole, and the rod-shaped part 102 can pass through the through hole. For example, the shielding member may be composed of two parts that are connected to facilitate the installation of the adjusting member.

Specifically, the tubular unit 1028 is sleeved on the rod-shaped part 102, an end of the tubular unit 1028 at least partially extends into the through hole and the opening 1024 of the adjusting member 1022, and a gap between the adjusting member 1022 and the rod-shaped part 102 and a gap between the through hole of the tubular unit 1028 and the rod-shaped part 102 can be filled, so as to prevent radiation from leaking from the gaps.

Specifically, an outer surface of the tubular unit 1028 away from an end of the through hole has a protruding shielding block 1029 in a radial direction. The shielding block 1029 is located within the groove of the base body. A diameter of the shielding block 1029 may be larger than a diameter of the tubular unit 1028, to achieve a better radiation shielding effect.

In the embodiment of the present disclosure, on the one hand, a gap position when the pull rod pushes the source carrier 107 from a source loading channel 1016 of the source guiding apparatus into a corresponding installation position of a radiotherapy device can be adjusted through the connector 101 or the adjusting member 1022 on the pull rod, thereby improving the flexibility and accuracy of the source replacement operation. On the other hand, the shielding member 1026 can be arranged to prevent radiation leakage and improve the safety of the source replacement operation.

In the embodiments of the present disclosure, directions are defined only with what is shown in the accompanying drawings as an example, and the sequence of specific steps of the source guiding method provided in the embodiments of the present disclosure is not limited.

In the description of the present disclosure, it should be understood that the directions or position relationships indicated by the terms, such as "center," "longitudinal," "transverse," "length," "width," "thickness," "above," "below," "front," "back," "left," "right," "vertical," "horizontal," "top," "bottom," "inner," "outer," "clockwise," and "counterclockwise," are based on the directions or position relationships shown in the accompanying drawings, are only provided to facilitate describing the present disclosure and simplifying the description, rather than indicating or implying that the apparatus or element referred to must have a specific direction, or be configured and operated in a specific direction, and therefore cannot be understood as limitations of the present disclosure.

In addition, the terms "first" and "second" are only used for the purpose of description, and cannot be understood as indicating or implying relative importance or implicitly indicating the number of indicated technical features. Thus, features defined with "first" or "second" may explicitly or implicitly include one or more of the features. In the description of the present disclosure, "plurality" means two or more than two, unless otherwise specifically defined.

In the present disclosure, unless otherwise clearly defined and limited, the terms, such as "installation," "connected," "connection," and "fixed," should be understood in a broad sense, for example, may be a fixed connection or a detachable connection, or an integration; may be a mechanical connection or an electrical connection; may be a direct connection, or an indirect connection through an intermediate medium, or may be an internal communication between two elements or an interaction relationship between two elements. For those of ordinary skills in the art, the specific meanings of the above terms in the present disclosure may be understood according to specific circumstances.

In the present disclosure, unless otherwise clearly defined and limited, the first feature "above" or "below" the second feature may include the first feature in direct contact with the second feature, or may include the first feature not being in direct contact with the second feature, but in contact with the second feature through other features between them. Further, the first feature "above" the second feature includes the first feature being right above and above the second feature, or merely indicates that the first feature is horizontally above the second feature. The first feature "below" the second feature includes the first feature being right below and below the second feature, or merely indicates that the first feature is horizontally below the second feature.

In the description of the present specification, descriptions with reference to the terms, such as "one embodiment," "some embodiments," "examples," "specific examples," or "some examples," mean that specific features, structures, materials, or characteristics described in conjunction with the embodiment or example are included in at least one embodiment or example of the present disclosure. In the present specification, schematic expressions of the above terms do not necessarily refer to the same embodiments or examples. In addition, the described specific features, structures, materials, or characteristics may be combined in any one or more embodiments or examples in a suitable manner. In addition, those skilled in the art may incorporate and combine different embodiments or examples described in the present specification.

After considering the specification and practicing the disclosure disclosed herein, those skilled in the art will easily think of other embodiments of the present disclosure. The present disclosure is intended to cover any variations, uses, or adaptive changes of the present disclosure. These variations, uses, or adaptive changes follow the general principles of the present disclosure and include common knowledge or conventional technical means in the technical field that is not disclosed in the present disclosure. The specification and the embodiments are only regarded as examples, and the true scope and spirit of the present disclosure are indicated by the appended claims.

What is claimed is:

1. A source storing apparatus, comprising: a source tank and a shielding plug, the source tank being provided with an opening and an accommodating cavity, the accommodating cavity being configured to accommodate a cobalt source box, the shielding plug being configured to seal an opening of the accommodating cavity; wherein
    a first connecting structure is provided on the cobalt source box;
    a second connecting structure is provided on an outer side of the shielding plug and
    a pickup structure is provided on an inner side of the shielding plug, and the first connecting structure is detachably connected to the pickup structure,
    wherein the first connecting structure is a connecting slot, the pickup structure is snappable into the connecting slot, the connecting slot comprises a first opening and a second opening that are in communication, wherein the first opening is in a first direction, and the second opening is in a second direction; and the pickup structure is configured to snap fit into the connecting slot through the first opening and get out of the connecting slot through the second opening.

2. The source storing apparatus according to claim 1, wherein the pickup structure is directly connected to the shielding plug; or the pickup structure is connected to the shielding plug through a connecting rod.

3. The source storing apparatus according to claim 1, wherein the connecting slot comprises a clamping slot and a compressing slot, wherein a maximum size of the clamping slot is larger than the first opening.

4. The source storing apparatus according to claim 3, wherein when the pickup structure comprises the elastic member, the first opening is larger than a minimum compression size of the elastic member and smaller than a maximum extension size of the elastic member.

5. The source storing apparatus according to claim 3, wherein a maximum size of the clamping slot is larger than the maximum extension size of the elastic member.

6. The source storing apparatus according to claim 3, wherein a maximum size of the compressing slot is smaller than the maximum extension size of the elastic member.

7. The source storing apparatus according to claim 1, wherein a bottom size of the second opening is larger than a top size of the second opening, and a maximum opening size of the second opening is larger than or equal to a minimum compression size of the pickup structure.

8. The source storing apparatus according to claim 4, wherein a size of the second opening at a position corresponding to the compressing slot is larger than or equal to the minimum compression size of the pickup structure.

9. A source guiding system, being configured to guide a cobalt source box from a first source storing apparatus into a second source storing apparatus, the cobalt source box further comprising a third connecting structure; and
    the source guiding system comprising: a source guiding tank, the source guiding tank comprising a tank body, a first pull rod and a first opening, a second pull rod and a second opening, wherein the tank body comprises a source-carrying cavity, the first pull rod and the first opening are located on opposite sides of the source-carrying cavity along a first direction, the second pull rod and the second opening are located on opposite sides of the source-carrying cavity along a second direction, the first pull rod moves along the first direction and is connectable to a second connecting structure of a shielding plug of the first source storing apparatus, a pickup structure of the shielding plug is detachably connected to a first connecting structure of the cobalt source box; and the second pull rod moves along the second direction and is connectable to the third connecting structure of the cobalt source box.

10. The source guiding system according to claim 9, further comprising a first shielding door configured to open and close the first opening; and/or
    the source guiding system further comprising a second shielding door configured to open and close the second opening.

11. The source guiding system according to claim 9, wherein the first direction is perpendicular to the second direction.

12. The source guiding system according to claim 9, wherein the first pull rod and/or the second pull rod are/is provided with a position restricting slot, and the source guiding system further comprises a fastener fixable with the position restricting slot to prevent the first pull rod and the second pull rod from rotating.

13. The source guiding system according to claim 9, wherein:
    a glass window is provided on the source guiding tank; or
    at least one of a camera or a detection lamp is further provided within the source-carrying cavity of the source guiding tank.

14. The source guiding system according to claim 9, wherein the source guiding tank comprises a plurality of components, and the plurality of components is fixedly connected.

15. A source guiding method, being used for guiding a cobalt source box from a source storing apparatus into a radiotherapy device, the method comprising:
- connecting a first connecting structure of the cobalt source box and a pickup structure of a shielding plug of the source storing apparatus;
- driving a first pull rod to connect the first pull rod to a second connecting structure of the shielding plug of the source storing apparatus, and lifting the shielding plug to a source-carrying cavity of a source guiding tank;
- driving a second pull rod to connect the second pull rod to a third connecting structure of the cobalt source box;
- driving the first pull rod to coordinate with the second pull rod, such that the first connecting structure of the cobalt source box separates from the pickup structure; and
- driving the second pull rod to enable the cobalt source box to enter the radiotherapy device and fix the cobalt source box with the radiotherapy device.

16. The method according to claim 15, wherein the driving the first pull rod to coordinate with the second pull rod, such that the first connecting structure of the cobalt source box separates from the pickup structure specifically comprises:
- driving the first pull rod to move along a first direction such that an elastic member is in a compressing slot; and
- driving the second pull rod to move along a second direction, such that the pickup structure is disengaged from a connecting slot through a second opening.

17. The method according to claim 16, further comprising: driving the radiotherapy device to switch off and shield a radioactive source.

18. A source guiding method, being applied to the source guiding system according to claim 9, wherein the first source storing apparatus is a radiotherapy device, the method comprising:
- driving the first pull rod to connect the first pull rod to the second connecting structure of the shielding plug of the second source storing apparatus, and lifting the shielding plug to the source-carrying cavity of the source guiding tank;
- driving the second pull rod to connect the second pull rod to the third connecting structure of the cobalt source box, and pulling the cobalt source box to the source-carrying cavity of the source guiding tank;
- driving the first pull rod to coordinate with the second pull rod, such that the first connecting structure of the cobalt source box is connected to the pickup structure;
- driving the second pull rod to separate the second pull rod from the cobalt source box; and
- driving the first pull rod to send the cobalt source box into the second source storing apparatus.

* * * * *